(12) United States Patent
Wagener et al.

(10) Patent No.: US 10,272,220 B2
(45) Date of Patent: *Apr. 30, 2019

(54) RESPIRATOR

(71) Applicant: Drägerwerk AG & Co. KGaA, Lübeck (DE)

(72) Inventors: Guido Wagener, Lübeck (DE); Gerald Panitz, Ellwangen (DE); Jens Köhne, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 872 days.

This patent is subject to a terminal disclaimer.

(21) Appl. No.: 14/851,817

(22) Filed: Sep. 11, 2015

(65) Prior Publication Data

US 2015/0374948 A1 Dec. 31, 2015

Related U.S. Application Data

(63) Continuation of application No. 13/474,157, filed on May 17, 2012, now Pat. No. 9,205,211.

(30) Foreign Application Priority Data

Nov. 11, 2011 (DE) .................. 10 2011 118 265

(51) Int. Cl.
*A61M 16/10* (2006.01)
*A61M 16/00* (2006.01)
*A61M 16/01* (2006.01)

(52) U.S. Cl.
CPC .......... *A61M 16/104* (2013.01); *A61M 16/00* (2013.01); *A61M 16/0003* (2014.02); *A61M 16/01* (2013.01); *A61M 16/024* (2017.08); *A61M 2016/003* (2013.01); *A61M 2016/0027* (2013.01); *A61M 2202/0241* (2013.01); *A61M 2205/3334* (2013.01); *A61M 2205/70* (2013.01); *A61M 2205/702* (2013.01); *A61M 2205/8212* (2013.01)

(58) Field of Classification Search
CPC ................ A61M 16/04; A61M 16/024; A61M 16/0003; A61M 16/01; A61M 16/00; A61M 16/022; A61M 16/0051; A61M 2205/8212; A61M 2205/70
See application file for complete search history.

(56) References Cited

U.S. PATENT DOCUMENTS

| | | |
|---|---|---|
| 4,819,629 A | 4/1989 | Jonson |
| 2002/0020410 A1 | 2/2002 | Rydin et al. |
| 2006/0090757 A1 | 5/2006 | Dittmann |
| 2009/0084381 A1 | 4/2009 | DeVries et al. |

*Primary Examiner* — Gregory A Anderson
*Assistant Examiner* — Margaret M Luarca
(74) *Attorney, Agent, or Firm* — McGlew and Tuttle, P.C.

(57) ABSTRACT

An breathing or anesthesia apparatus and a process for operating a breathing or anesthesia apparatus are provided in which only a very low energy consumption occurs outside of the operating times. The breathing or anesthesia apparatus (1) is put into an energy-saving mode and a function pretest is performed before putting the apparatus into the energy-saving mode. A function self-test is carried out when the breathing or anesthesia apparatus is put into a standby mode.

20 Claims, 3 Drawing Sheets

RESPIRATOR

CROSS REFERENCE TO RELATED APPLICATIONS

This is a Continuation of application Ser. No. 13/474,157, filed on May 17, 2012, which claims the benefit of priority under 35 U.S.C. § 119 of DE 10 2011 118 265.2 filed Nov. 11, 2011, the entire contents of which are incorporated herein by reference.

FIELD OF THE INVENTION

The present invention pertains to a breathing or anesthesia apparatus for the artificial respiration of a patient, comprising a gas delivery means, a gas line, an operating unit to operate and/or control the breathing or anesthesia apparatus, and a control unit, and to a process for operating a breathing and anesthesia apparatus.

BACKGROUND OF THE INVENTION

Artificial respiration of patients is necessary for various medical applications, e.g., during surgery. Breathing apparatuses without rebreathing are used for the artificial respiration of patients in intensive care units of hospitals. The expired gas breathed out by the patient is reused as inspiration gas in anesthesia apparatuses, i.e., this is a rebreathing system with breathing air circulation. A gas delivery means, which sends the breathing air to the patient during inspiration, is present in the breathing air circulation system in the anesthesia apparatus. The gas delivery means is either switched off or is being operated with a very low output only during and after expiration.

A self-test is to be performed in breathing or anesthesia apparatuses before the beginning of use of the apparatus. Reliable function of the breathing or anesthesia apparatus shall be guaranteed hereby. Such a self-test requires an overall duration of 8 minutes, which leads to an increased burden in terms of time for the staff performing this task. An essentially shorter pretest, during which only the essential components of the breathing or anesthesia apparatus are tested is performed for this reason before the self-test proper. As a result, obvious errors shall be recognized early on rather than being displayed only after the more prolonged self-test. Obvious errors can be recognized by the user during the pretest and subsequently corrected.

Outside the operating times of the breathing or anesthesia apparatus, the apparatus is put into a so-called standby mode. Only certain functions of the apparatus, e.g., a monitor of an input unit, are temporarily deactivated in the standby mode, but the breathing or anesthesia apparatus can be briefly set again into full operating functionality. A processor or a computing unit of the control unit is switched on during the standby mode, and a heating means of the breathing or anesthesia apparatus is also switched on during the standby mode, so that the power consumption may definitely be 70 W in the standby mode. Thus, the breathing or anesthesia apparatus has a high electric power consumption during the standby mode outside the operating times of the breathing or anesthesia apparatus, e.g., during the night, and the breathing or anesthesia apparatus disadvantageously has a high energy consumption as a result.

US 2008//0147136 A1 shows a process and a device for the automatic self-test of medical devices. It is detected with this process whether the medical device has reached the time for an automatic self-test when the medical device is in a switched-off state. If the result that is detected is positive, an automatic self-test is performed.

SUMMARY OF THE INVENTION

An object of the present invention is therefore to provide a breathing or anesthesia apparatus and a process for operating a breathing or anesthesia apparatus, in which the breathing or anesthesia apparatus has only a very low energy consumption outside the operating times and the standby state can be obtained reliably with a low risk of failure.

This object is accomplished with a breathing or anesthesia apparatus for the artificial respiration of a patient, comprising a gas delivery means, at least one gas line for forming a breathing air line system, especially a breathing air circulation system, an operating unit for operating and/or controlling the breathing or anesthesia apparatus, a control unit, wherein a process described herein can be carried out with the device.

The breathing or anesthesia apparatus comprises an inspiration tube and an expiration tube and/or the breathing or anesthesia apparatus has a Y-piece, wherein said inspiration tube and an expiration tube are connected to the Y-piece.

In one embodiment, the breathing or anesthesia apparatus comprises a heating means. Components within the breathing or anesthesia apparatus, e.g., a gas line, and/or the inspiration and/or expiration tube, are warmed or heated by means of the heating means in order to guarantee proper function, especially in order to prevent condensation of water, which is contained in the breathing air, in the breathing or anesthesia apparatus. The operating unit preferably comprises in this case a monitor and/or input members, e.g., keys, so that the breathing or anesthesia apparatus can be brought or switched into different operating states thereby.

In a process according to the present invention for operating a breathing or anesthesia apparatus, a self-test and a pretest are performed, and the pretest is carried out before the self-test, and the breathing or anesthesia apparatus is put into an energy-saving mode and the pretest is carried out before putting into the energy-saving mode. The breathing or anesthesia apparatus requires an especially small amount of energy, especially a small amount of electric power in the energy-saving mode, and the breathing or anesthesia apparatus has already been tested before the energy-saving mode by a pretest, so that the risk of occurrence of errors is very low after ending the energy-saving mode and after putting the apparatus into a standby mode because the essential components had already been tested in a pretest before the energy-saving mode.

The pretest is performed by a control unit compulsorily before setting the energy-saving mode obligatorily and/or automatically, so that the pretest will have been performed as a result before each energy-saving mode and it will especially have been performed successfully because the energy-saving mode is only carried out in case of a successful pretest, so that the essential components of the breathing or anesthesia apparatus are already tested as a result after ending the energy-saving mode. In case of an error in the pretest, this is displayed to the user and the user can correct the error, so that when the pretest is carried out once again, it is carried out successfully.

The self-test is preferably carried out after the end of the energy-saving mode and/or before a standby mode, and the breathing or anesthesia apparatus is put into a standby mode after a successful self-test. Before the breathing or anesthesia apparatus is put into the standby mode, the self-test will thus have been carried out, and all components of the breathing or anesthesia apparatus will have been tested with the self-test as a result. This makes possible reliable operation of the breathing or anesthesia apparatus in the standby mode. Furthermore, the risk of occurrence of errors in the self-test is very low because the essential components of the breathing or anesthesia apparatus will have already been tested in the pretest before the energy-saving mode.

The pretest is advantageously carried out obligatorily and/or automatically before the breathing or anesthesia apparatus is put into the standby mode. The pretest is thus carried out automatically before the standby mode, and the breathing or anesthesia apparatus will thereby have been tested completely with the self-test when in the standby mode.

More components are tested in the self-test than in the pretest, and the pretest takes less time than does the self-test. The pretest is carried out within about 1-2 minutes, while the overall duration of the self-test is about 8 minutes.

In particular, connections and settings to be performed by the user, whose absence or incorrect performance would thwart the successful completion of the self-test, are tested in the pretest. For example, the presence of gas supply means and power supply means and/or the correct setting of valves, for example, of an APL valve (Adjustable Pressure Limiting Valve) on a breathing air circulating system, and/or the correct correction and sealing of breathing gas tubes and the Y-piece located thereon are tested. The things that are frequently overlooked by the user are tested in the pretest.

All the checks, calibrations and measurements, such as the calibration of pressure sensors, calibration of flow sensors, measurement of leaks from the breathing air circulation system and connected tubes are carried out with full precision and hence also with a long time requirement in the self-test.

In another embodiment, the point in time at which the standby mode is reached is entered into an operating unit, and the self-test is performed depending on the point in time entered. The user of the breathing or anesthesia apparatus can thus indicate a point in time, e.g., also separately for a weekday with a calendar function, so that the breathing or anesthesia apparatus is in the standby mode at a certain time, e.g., at 7 a.m. If the self-test requires, e.g., 8 minutes and 7 o'clock is set as the time for the standby mode, the self-test is performed automatically by the breathing or anesthesia apparatus 8 minutes before 7 o'clock. Unlike in this case, the apparatus may also be put into the standby mode from the energy-saving mode without presetting a time for the standby mode by the user entering corresponding inputs on the operating unit. Only the 8 minutes for the self-test are needed in this case until the apparatus enters the standby mode after conclusion of the self-test.

The power consumption of the breathing or anesthesia apparatus is less than 20 W, 10 W, 5 W or 3 W during the energy-saving mode and/or electric components, especially a heating means, are switched off at least partly and especially completely during the energy-saving mode. Thus, the breathing or anesthesia apparatus requires an especially small amount of energy during the energy-saving mode. The breathing or anesthesia apparatus is put into the energy-saving mode outside the regular operating times, e.g., during the night or on the weekend, and energy can be saved with the breathing or anesthesia apparatus as a result, because the breathing or anesthesia apparatus requires very little energy outside the operating times.

The present invention also comprises a computer program, which is stored on a computer-readable data storage medium, in order to carry out a process as described when the computer program is run on a computer or a corresponding computing unit or a control unit.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
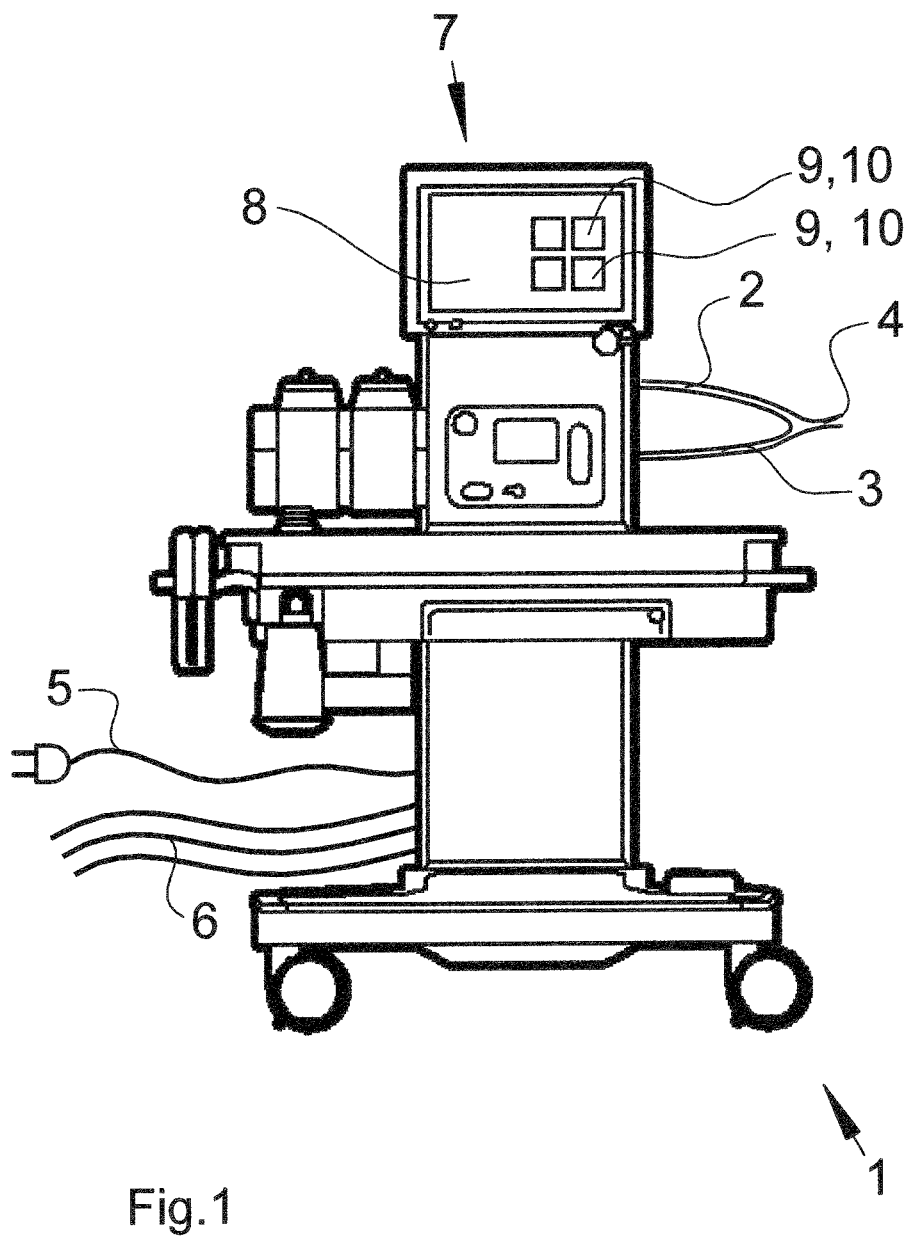
FIG. 1 is a simplified view of a breathing or anesthesia apparatus according to the invention.

Referring to the drawings in particular, FIG. 1 shows a breathing or anesthesia apparatus 1. The anesthesia apparatus 1 has a breathing air circulation system, so that expired gas breathed out by the patient can be reused as inspiration gas. The inspiration gas fed to the patient to be breathed is fed to the patient through an inspiration tube 2, which is a part of a breathing air line system, designed especially as a breathing air circulation system here. After flowing through the inspiration tube and a Y-piece 4, the inspiration gas is fed to the patient through a tube, not shown in greater detail. The air breathed out by the patient is removed as expiration gas through an expiration tube 3. The anesthesia apparatus 1 can be connected to the power supply network of the hospital with a power connection cable 5. In addition, the anesthesia apparatus 1 has gas supply lines 6 for connection to a central gas supply of the hospital.

The breathing or anesthesia apparatus 1 has an operating unit 1. The operating unit 7 comprises a monitor 8 for the optical display of operating states as well as a plurality of input members 9, which are designed as keys 10.

Figure 2:
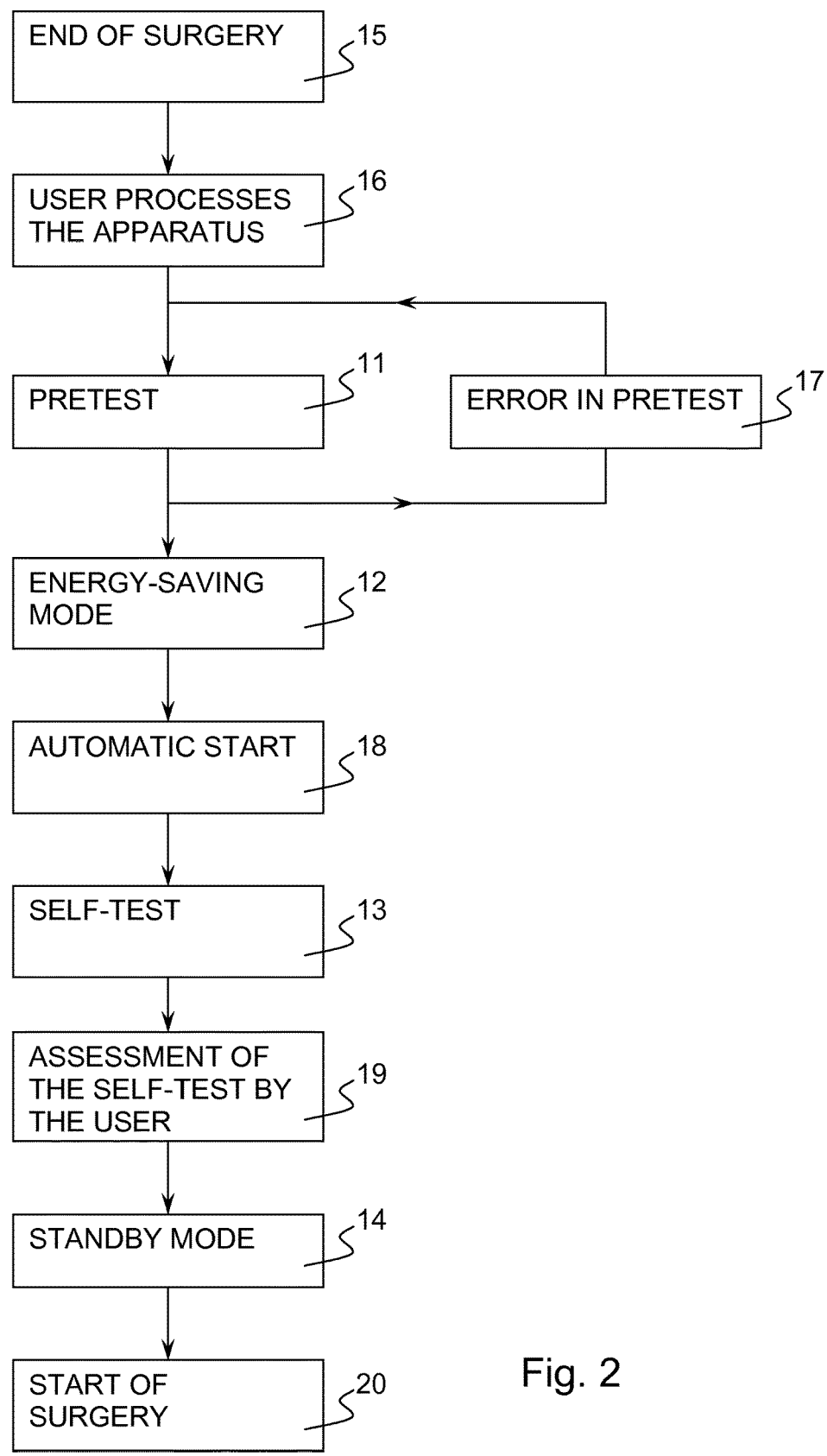
FIG. 2 is a view showing process steps of a process according to the invention for operating the breathing or anesthesia apparatus.

FIG. 2 shows process steps of a process for operating the breathing or anesthesia apparatus 1 or program steps of the process. A patient, not shown, is artificially respirated or anesthetized during a surgery with the breathing or anesthesia apparatus 1. After the end of a surgery, i.e., an end of surgery 15, the breathing or anesthesia apparatus 1 is not needed any longer, and the user performs a processing 16 of the breathing or anesthesia apparatus 1 in a further step. For example, there is an end of service—end of service processing—when the breathing or anesthesia apparatus 1 is not needed any longer during the night. This is entered on the operating unit 7 by the user and the breathing or anesthesia apparatus automatically performs a pretest 11. Only the essential components of the breathing or anesthesia apparatus 1 are tested in the pretest 11, which takes, e.g., only 1 minute. If no errors occur in the pretest 11, the apparatus is put automatically into an energy-saving mode 12 by a control unit 30. However, if errors 17 occurred during the pretest 11, this is displayed to the user visually and/or audibly and the user is prompted thereby to correct the errors 17 recognized in the pretest 11. It is only subsequently and after correction of these errors 17 that the pretest 11 is carried out until no errors 17 occur during the pretest 11, and the apparatus 1 is put into the energy-saving mode 12 only thereafter. In the energy-saving mode 12 there is a very low electric energy consumption, e.g., less than 2 W. A heating means 32 of the breathing or anesthesia apparatus 1 is switched off, and a computing unit of the control unit 30 is also put into an energy-saving mode or is switched off altogether. Before the apparatus is put into the energy-saving mode 12, e.g., already when entering the fact that the breathing or anesthesia apparatus 1 is to be put into the energy-saving mode 12, the user enters the time when there again will be a need for the breathing or anesthesia apparatus 1 after the end of the energy-saving mode 12, e.g., at 7 o'clock on the next day. If the user enters, for example, that the user would need the breathing or anesthesia apparatus 1 again after the end of the energy-saving mode 12, e.g., at 7 o'clock on the next day, a self-test 13 is carried out by the control unit 30 of the breathing or anesthesia apparatus 1 automatically and independently at a time sufficiently before the requested standby mode 14. If a standby mode 14 at 7 o'clock is entered and the duration of the self-test 13 is, e.g., 8 minutes, the self-test 13 is started 8 minutes before 7 o'clock, so that the breathing or anesthesia apparatus 1 is in the standby mode 14 at 7 o'clock in case of a successful self-test 13.

Pretest 11 is carried out before putting into the energy-saving mode 12, so that when the breathing or anesthesia apparatus 1 is put from the energy-saving mode 12 into the standby mode 14 and during the self-test 13 inserted in-between, no errors will occur, as a rule, in the self-test 13, because the essential components of the breathing or anesthesia apparatus 1 had already been tested in the pretest 11 and errors that were possibly present will have already been corrected by the user. The point in time of the standby mode 14 can also be entered by the user by means of a calendar function, for example, such that the standby mode 14 has to be present beginning from 7 o'clock on workdays from Monday up to and including Friday and no standby mode 14 is necessary on Saturdays and Sundays. The self-test 13 is thus carried out after an automatic start 18 of the breathing or anesthesia apparatus 1 and an assessment 19 of the self-test 13 is performed by the user after the end of the self-test 13. If no errors of the self-test 13 are displayed by the operating unit 7, artificial respiration and anaesthetization of the patient can again be started, i.e., a surgery 20 can be started.

Figure 3:
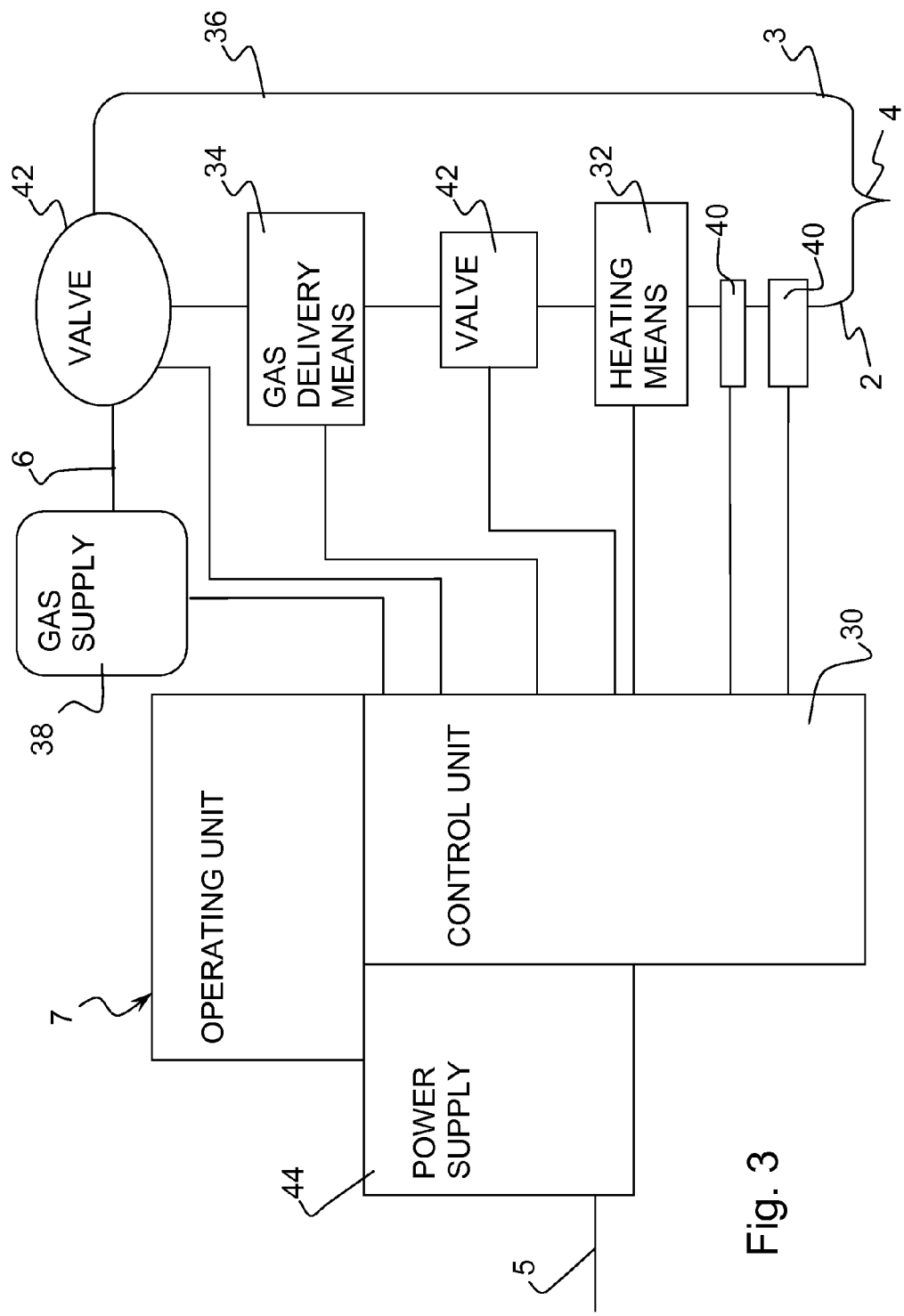
FIG. 3 is a schematic view showing aspects of the breathing or anesthesia apparatus according to the invention.

FIG. 3 provides a schematic representation of the breathing or anesthesia apparatus 1 for the artificial respiration of a patient. The control unit 30 is shown connected to the operating unit 7 as well as to a power supply 44. The power supply 44 is connected to all of the various powered components including the heating means 32. A breathing gas circulation system 36 with the inspiration tube 2, the Y-piece 4 and the expiration tube 3, parts of a breathing air line system, is warmed or heated by means of the heating means 32 in order to guarantee proper function, especially in order to prevent condensation of water. The breathing gas circulation system 36 has a gas delivery means 34. The breathing or anesthesia apparatus 1 also includes one or more gas supplies 38, valves 42 and sensors 40. The sensors 40 may include flow sensors, temperature sensors, and sensors of the composition of the breathing gas and may also include sensors to detect the connection of various components such as the connection of the Y-piece 4 to the inspiration tube 2 and expiration tube 3, connection of the gas supply via one or more supply lines 6 and connection of the power supply 44 to the power supply network of the hospital via the power connection cable 5.

On the whole, essential advantages are associated with the breathing or anesthesia apparatus 1 according to the present invention and with the process according to the present invention for operating the breathing or anesthesia apparatus 1. Outside a necessary standby mode 14, i.e., during the night and on weekends, the breathing or anesthesia apparatus 1 is in an energy-saving mode 12, in which the breathing or anesthesia apparatus 1 requires only very little electricity. As a result, the need for electric energy for the breathing or anesthesia apparatus 1 can be substantially reduced. Furthermore, the pretest 11 is obligatorily performed before the breathing or anesthesia apparatus is put into the energy-saving mode, so that no errors occur, as a rule, during the self-test 13 performed independently before the standby mode 14, because obvious errors or defects of the breathing or anesthesia apparatus 1 will have already been tested in the pretest 11 and possibly corrected by the user.

While specific embodiments of the invention have been shown and described in detail to illustrate the application of the principles of the invention, it will be understood that the invention may be embodied otherwise without departing from such principles.

APPENDIX

LIST OF REFERENCE NUMBERS

1 Breathing or anesthesia apparatus
2 Inspiration tube
3 Expiration tube
4 Y-piece
5 Power connection cable
6 Gas supply lines
7 Operating unit
8 Monitor
9 Input members
10 Key
11 Pretest
12 Energy-saving mode
13 Self-test
14 Standby mode
15 End of surgery
16 User processes the apparatus
17 Error in pretest
18 Automatic start
19 Assessment of the self-test by the user
20 Start of surgery
30 Control unit
32 Heating means
34 Gas delivery means
36 Breathing gas circulation system
38 Gas supply
40 Sensors
42 Valves
44 Power supply

What is claimed is:

1. A breathing or anesthesia apparatus for the artificial respiration of a patient, the apparatus comprising:
   a gas delivery means;
   a breathing air line system comprising a gas line;
   an operating unit to operate and/or control the breathing or anesthesia apparatus; and
   a control unit for initiating a self-test and a pretest wherein the pretest is carried out before the self-test, wherein said control unit puts the breathing or anesthesia apparatus into an energy-saving mode and a standby mode, the energy saving mode using less power than the standby mode, said control unit automatically performs the pretest before putting the breathing or anesthesia apparatus into the energy-saving mode;

said control unit automatically performs the self-test after the end of the energy-saving mode.

2. A breathing or anesthesia apparatus in accordance with claim 1, wherein:
said control unit performs the self-test before the control unit puts the breathing or anesthesia apparatus into the standby mode.

3. A breathing or anesthesia apparatus in accordance with claim 1, wherein:
the pretest is carried out as an obligatorily action before putting the breathing or anesthesia apparatus into the energy-saving mode.

4. A breathing or anesthesia apparatus in accordance with claim 3, wherein the self-test is carried out as an obligatorily action before the breathing or anesthesia apparatus is put into the standby mode.

5. A breathing or anesthesia apparatus in accordance with claim 1, wherein more parameters or components of the breathing or anesthesia apparatus are tested in the self-test than in the pretest.

6. A breathing or anesthesia apparatus in accordance with claim 1, further comprising one or more gas supplies, one or more power supplies and sensors, wherein:
a presence of the one or more gas supplies and the one or more power supplies is tested by the control unit in the pretest; and/or
a calibration of the sensors is carried out by the control unit in the self-test.

7. A breathing or anesthesia apparatus in accordance with claim 1, wherein:
a point in time at which the standby mode is to be reached is entered with the operating unit; and
a point in time that the self-test is to be carried out as a function of said point in time at which the standby mode is to be reached is entered with the operating unit or is calculated by the control unit.

8. A process for operating a breathing or anesthesia apparatus, the process comprising the steps of:
providing a breathing or anesthesia apparatus with a gas delivery means, a breathing air line system comprising a gas line, an operating unit to operate and/or control the breathing or anesthesia apparatus, and a control unit for initiating a self-test and a pretest and an energy-saving mode and a standby mode, the energy saving mode using less power than the standby mode;
carrying out the self-test and the pretest with the breathing or anesthesia apparatus in which the pretest is carried out before the self-test; and
putting the breathing or anesthesia apparatus into the energy-saving mode and automatically carrying out the pretest before putting the breathing or anesthesia apparatus into the energy-saving mode;
automatically performing the self-test after the end of the energy-saving mode.

9. A process in accordance with claim 8, wherein:
the self-test is performed before the breathing or anesthesia apparatus is operated in the standby mode.

10. A process in accordance with claim 8, wherein:
automatically changing operation of the breathing or anesthesia apparatus from the pretest to the energy saving mode after the pretest is finished, and before operation of the breathing or anesthesia apparatus changes from the pretest to the standby mode.

11. A process in accordance with claim 8, wherein the pretest is carried out as an obligatorily action and/or automatically before putting the breathing or anesthesia apparatus into the energy-saving mode.

12. A process in accordance with claim 8, wherein the energy saving mode is carried out as an obligatorily action and/or automatically before putting the breathing or anesthesia apparatus into the standby mode.

13. A process in accordance with claim 8, wherein the self-test is carried out as an obligatorily action before the breathing or anesthesia apparatus is put into the standby mode.

14. A process in accordance with claim 8, wherein more parameters or components of the breathing or anesthesia apparatus are tested in the self-test than in the pretest.

15. A process in accordance with claim 8, wherein:
the provided breathing or anesthesia apparatus comprises one or more gas supplies, one or more power supplies and sensors;
the presence of the one or more gas supplies and the one or more power supplies is tested in the pretest; and/or
a calibration of the sensors is carried out in the self-test.

16. A process in accordance with claim 8, wherein:
a point in time at which the standby mode is to be reached is entered with the operating unit; and
a point in time that the self-test is to be carried out is calculated by the control unit or entered into the operating unit as a function of the point in time at which the standby mode is to be reached.

17. A process for operating a breathing or anesthesia apparatus, the process comprising the steps of:
providing a breathing or anesthesia apparatus;
operating the breathing or anesthesia apparatus in a respiration mode wherein the breathing or anesthesia apparatus provides breathing gas to a patient for respiration;
operating the breathing or anesthesia apparatus in a standby mode wherein the breathing gas is not provided to the patient;
operating the breathing or anesthesia apparatus in energy saving mode wherein the apparatus is less operational than the standby mode, the energy saving mode using less power than the respiration mode and the standby mode;
operating the breathing or anesthesia apparatus in a pretest mode wherein a first plurality of functions of the breathing or anesthesia apparatus is tested;
operating the breathing or anesthesia apparatus in a self test mode wherein a second plurality of functions of the breathing or anesthesia apparatus is tested, the second plurality of functions being different than the first plurality of functions;
automatically changing operation of the breathing or anesthesia apparatus from the pretest mode to the energy saving mode after testing of the first plurality of functions of the breathing or anesthesia apparatus is finished.

18. A process in accordance with claim 17, wherein:
said changing from the pretest mode to the energy saving mode is performed before operation of the breathing or anesthesia apparatus changes from the pretest mode to the standby mode.

19. A process in accordance with claim 17, wherein:
said changing from the pretest mode to the energy saving mode is performed before operation of the breathing or anesthesia apparatus changes from the pretest mode to the self test mode.

20. A process in accordance with claim 17, further comprising:

automatically changing operation of the breathing or anesthesia apparatus from the energy saving mode to the self test mode before operation of the breathing or anesthesia apparatus changes from the energy saving mode to the standby mode;

automatically changing operation of the breathing or anesthesia apparatus from the self test mode to the standby mode when testing of the second plurality of functions of the breathing or anesthesia apparatus is finished.

\* \* \* \* \*